United States Patent
Han

(10) Patent No.: US 9,135,377 B2
(45) Date of Patent: Sep. 15, 2015

(54) METHODS AND SYSTEMS FOR CREATING A COMPUTERIZED MODEL CONTAINING POLYDISPERSE SPHERICAL PARTICLES PACKED IN AN ARBITRARILY-SHAPED VOLUME

(75) Inventor: Zhidong Han, Livermore, CA (US)

(73) Assignee: Livermore Software Technology Corp., Livermore, CA (US)

( * ) Notice: Subject to any disclaimer, the term of this patent is extended or adjusted under 35 U.S.C. 154(b) by 727 days.

(21) Appl. No.: 13/447,696

(22) Filed: Apr. 16, 2012

(65) Prior Publication Data

US 2013/0275090 A1    Oct. 17, 2013

(51) Int. Cl.
  G06F 17/50    (2006.01)
  G06F 19/00    (2011.01)

(52) U.S. Cl.
  CPC .......... G06F 17/5009 (2013.01); G06F 19/701 (2013.01); G06F 2217/16 (2013.01)

(58) Field of Classification Search
  CPC ............ G05F 2217/41; G05F 2217/44; G05F 2217/38; G05F 19/701
  See application file for complete search history.

(56) References Cited

U.S. PATENT DOCUMENTS

| | | | | |
|---|---|---|---|---|
| 5,581,468 A * | 12/1996 | White et al. | .................. | 700/204 |
| 7,257,490 B2 * | 8/2007 | Georgi et al. | .................... | 702/11 |
| 7,349,832 B2 * | 3/2008 | Anderson | .......................... | 703/9 |
| 7,363,161 B2 * | 4/2008 | Georgi et al. | ..................... | 702/7 |
| 7,415,398 B2 * | 8/2008 | Naito et al. | ........................ | 703/6 |
| 8,635,050 B2 * | 1/2014 | Aikawa | ............................. | 703/2 |
| 2002/0010570 A1 * | 1/2002 | Malthe-Sorenssen et al. | . | 703/10 |
| 2002/0128777 A1 * | 9/2002 | Fanini et al. | ..................... | 702/11 |
| 2003/0097244 A1 * | 5/2003 | Davis et al. | ....................... | 703/6 |
| 2004/0088145 A1 * | 5/2004 | Rosenthal et al. | ................ | 703/1 |
| 2005/0086034 A1 * | 4/2005 | Naito et al. | ........................ | 703/2 |
| 2007/0203677 A1 * | 8/2007 | Awwiller | .......................... | 703/1 |
| 2008/0193739 A1 * | 8/2008 | Dickey et al. | ............. | 428/317.9 |
| 2009/0204377 A1 * | 8/2009 | Van Wagoner et al. | .......... | 703/9 |
| 2010/0042386 A1 * | 2/2010 | Milne | ............... | 703/6 |

(Continued)

OTHER PUBLICATIONS

Close packing density of Polydispersed hard Spheres by Farr et al (2009) pp. 1-8.*

(Continued)

Primary Examiner — Akash Saxena
(74) Attorney, Agent, or Firm — Roger H. Chu

(57) ABSTRACT

Systems and methods for creating a computerized model containing polydisperse spherical particles packed in an arbitrarily-shaped volume are disclosed. To create the computerized model, a plurality of polydisperse spherical particles having statistical properties according the characteristic profile (e.g., minimum and maximum sizes and size distribution) is generated. First portion of the particles is used for forming a border layer within the volume's boundary. Any hole in the border layer is sealed with one or more null-sized particles. Second portion of the particles is used for filling up an interior space in a layer-to-layer scheme from the border layer inwards. The layer-to-layer scheme includes searching a best suitable location from a list of size-ranked candidate locations using power diagrams. Each of the second portion of the particles is allowed to pass through holes in the current layer towards the border layer when possible.

14 Claims, 19 Drawing Sheets

(56) References Cited

U.S. PATENT DOCUMENTS

| | | | |
|---|---|---|---|
| 2010/0103977 A1* | 4/2010 | Kono et al. | 374/57 |
| 2010/0169062 A1* | 7/2010 | Linn et al. | 703/2 |
| 2011/0032255 A1* | 2/2011 | Favier et al. | 345/420 |
| 2011/0270594 A1* | 11/2011 | Rudnicki | 703/2 |
| 2012/0179426 A1* | 7/2012 | Fontes et al. | 703/1 |
| 2012/0253756 A1* | 10/2012 | Favier | 703/2 |
| 2013/0238302 A1* | 9/2013 | Ueno | 703/6 |
| 2014/0142890 A1* | 5/2014 | Daigle et al. | 702/157 |
| 2014/0290531 A1* | 10/2014 | Jaeger et al. | 106/400 |
| 2014/0379313 A1* | 12/2014 | Ueno | 703/2 |

OTHER PUBLICATIONS

Simulation of random packing of polydisperse particles by Riyadh Al-Raoush et al, Powder Technology 176 (2007), pp. 47-55.*

Effect of particle size distribution and packing compression on fluid permeability as predicted by lattice-Boltzmann simulations by David Vidala et al, Computers and Chemical Engineering 33 (2009) 256-266.*

A dissipative particle dynamics method for modeling the geometrical packing of filler particles in polymer composites by JA Elliot et al, Journal of Chemical Physics vol. 113, No. 22 Dec. 8, 2000, pp. 10367-10376.*

* cited by examiner

METHODS AND SYSTEMS FOR CREATING A COMPUTERIZED MODEL CONTAINING POLYDISPERSE SPHERICAL PARTICLES PACKED IN AN ARBITRARILY-SHAPED VOLUME

FIELD

The present invention generally relates to creation of a computerized model in a computer aided engineering analysis for numerical simulation of a product, more particularly to methods and systems for creating a computerized model representing polydisperse spherical particles packed in an arbitrarily-shaped volume.

BACKGROUND

Many modern engineering analyses are performed with the aid of a computer system. One of such computer aided engineering (CAE) analyses is referred to as discrete element method (DEM) or distinct element method, which is generally used for numerically simulating the motion of a large number of particles. With advances in computing power and numerical algorithms for nearest neighbor sorting, it has become possible to numerically simulate millions of particles. Today DEM is becoming widely accepted as an effective method of addressing engineering problems in granular and discontinuous materials, especially in granular flows, powder mechanics, and rock mechanics.

Since DEM requires large number of particles, efficient creation of initial computerized model is critical to the success of a simulation. Otherwise, an infeasible amount of time would be required to generate such model. Prior art approaches for creation such computerized model are based on methods having drawbacks. For example, geometric method lacks of packing density, sedimentation method requires a dropping direction as a Priori (for an arbitrarily-shaped volume, there isn't one) and dynamic method (similar to molecular dynamics) is too slow due extensive computation requirements.

It would therefore be desirable to have methods and systems for efficiently and effectively creating a computerized model containing polydisperse spherical particles packed in an arbitrarily-shaped volume.

SUMMARY

This section is for the purpose of summarizing some aspects of the present invention and to briefly introduce some preferred embodiments. Simplifications or omissions in this section as well as in the abstract and the title herein may be made to avoid obscuring the purpose of the section. Such simplifications or omissions are not intended to limit the scope of the present invention.

Systems and methods for creating a computerized model containing polydisperse spherical particles packed in an arbitrarily-shaped volume are disclosed. According to one aspect of the present invention, a definition of an arbitrarily-shaped volume (e.g., in form of polygons representing the volume's boundary), characteristic profile (e.g., maximum and minimum sizes and distribution) of the polydisperse spherical particles and desired packing requirements are received in a computer system.

A computerized model is then created using a plurality of polydisperse spherical particles, which is generated in accordance with the characteristic profile such that the plurality of polydisperse spherical particles possesses statistical properties defined in the characteristic profile.

First portion of the particles is used for forming a border layer within the volume's boundary disposed onto the polygons. In the border layer, any hole or space is "sealed" with one or more null-sized particles. After the border layer has been formed and sealed, a second portion of the particles is used for filling up an interior space surrounded by the border layer in a layer-to-layer scheme from the border layer inwards. The layer-to-layer scheme includes searching a best suitable location from a list of candidate locations. The list of candidate locations is identified using three-dimensional power diagrams and ranked by respective sizes of the candidate locations. Each of the second portion of the particles is allowed to pass through holes or spaces in the current layer towards the border layer when possible.

According to another aspect, each of the polygons representing the volume's boundary is configured for have a directionality property for indicating interior side of the volume.

According to still another aspect, forming of the border layer is performed by placing the generated particles near vertexes of each polygon, along edges of each polygon and the inner space bound by already-placed particles.

Objects, features, and advantages of the present invention will become apparent upon examining the following detailed description of an embodiment thereof, taken in conjunction with the attached drawings.

BRIEF DESCRIPTION OF THE DRAWINGS

These and other features, aspects, and advantages of the present invention will be better understood with regard to the following description, appended claims, and accompanying drawings as follows:

DETAILED DESCRIPTION

In the following description, numerous specific details are set forth in order to provide a thorough understanding of the present invention. However, it will become obvious to those skilled in the art that the present invention may be practiced without these specific details. The descriptions and representations herein are the common means used by those experienced or skilled in the art to most effectively convey the substance of their work to others skilled in the art. In other instances, well-known methods, procedures and components have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Embodiments of the present invention are discussed herein with reference to FIGS. 1-11. However, those skilled in the art will readily appreciate that the detailed description given herein with respect to these figures is for explanatory purposes as the invention extends beyond these limited embodiments.

Figure 1:
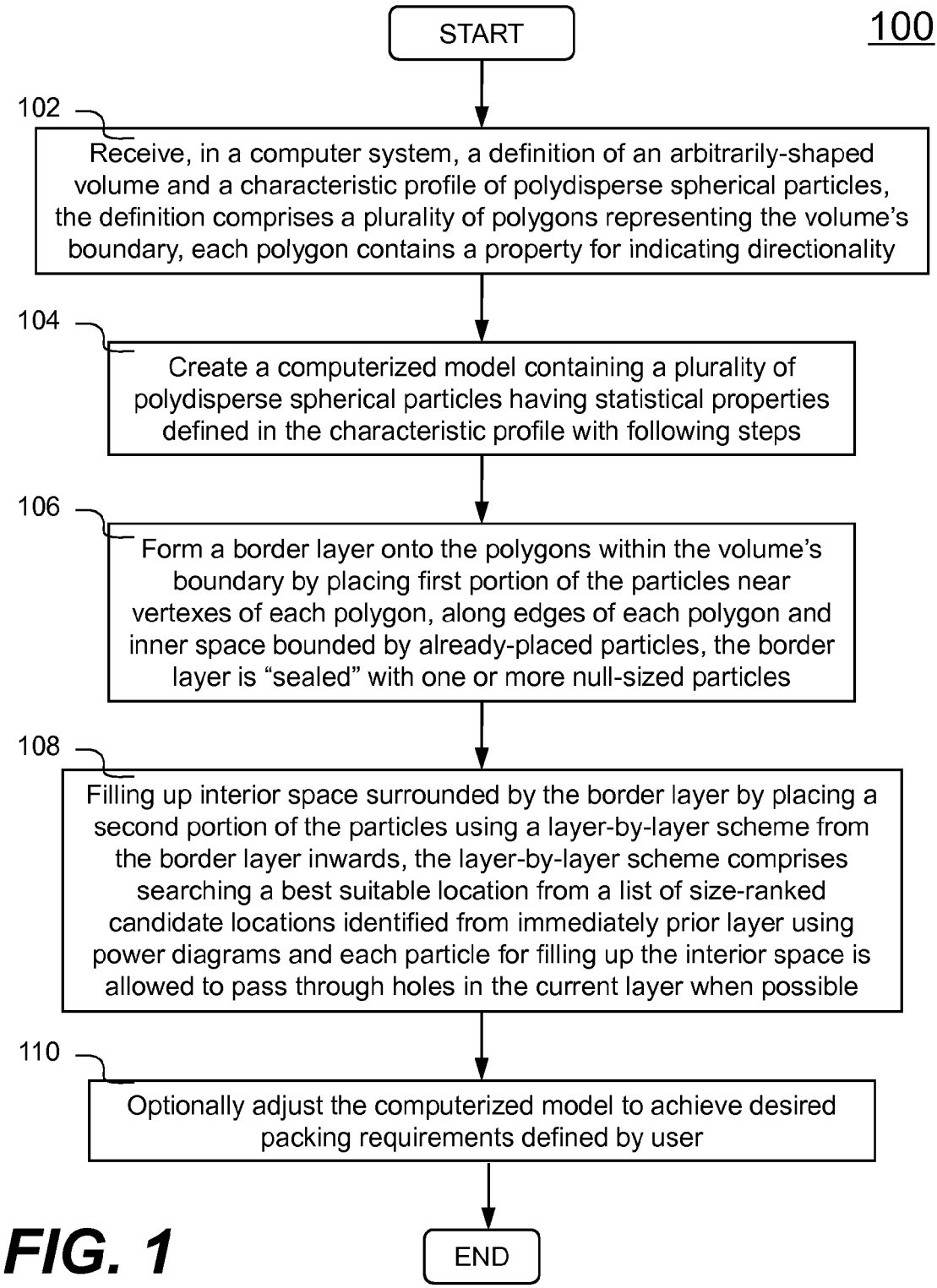
FIG. 1 is a flowchart illustrating an exemplary process of creating a computerized model containing a plurality of polydisperse spherical particles packed in an arbitrarily-shaped volume, according to an embodiment of the present invention.

FIG. 1 is a flowchart illustrating an exemplary process 100 of creating a computerized model containing a plurality of polydisperse spherical particles packed in an arbitrarily-shaped volume, according to an embodiment of the present invention. Process 100 is implemented in software and preferably understood with other figures.

Process 100 starts by receiving, in a computer system (e.g., computer system 1100 of FIG. 11), a definition of an arbitrarily-shaped volume and a characteristic profile of polydisperse spherical particles at step 102.

One exemplary definition of arbitrarily-shaped volume is a CAE mesh model containing a plurality of polygons (e.g., triangles, quadrilaterals, pentagons, etc.), which represents the volume's boundary. Each polygon is configured for containing a directionality property that indicates which side of the polygon is the inside or outside of the volume. This can be accomplished with a number of well-known methods, One exemplary method is to have a normal vector out of the plane the polygon is located on. The inside direction is either positive or negative normal vector. For a triangular polygon 512 shown in FIG. 5A, a normal vector can be defined by applying a right-hand rule to the ordered vertexes 501-503. In other words, the normal vector is perpendicular to polygon 512.

Figure 2A:
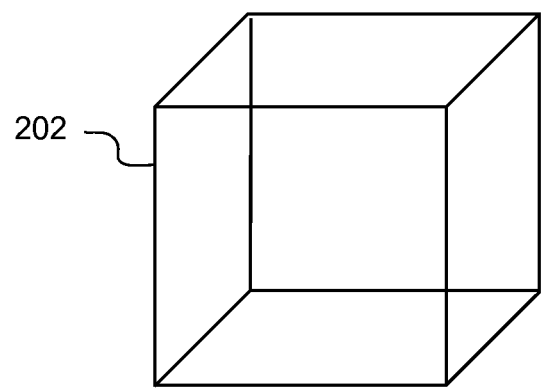
FIGS. 2A-2B are diagrams showing various exemplary arbitrarily-shaped volume in accordance with one embodiment of the present invention.
Figure 2B:
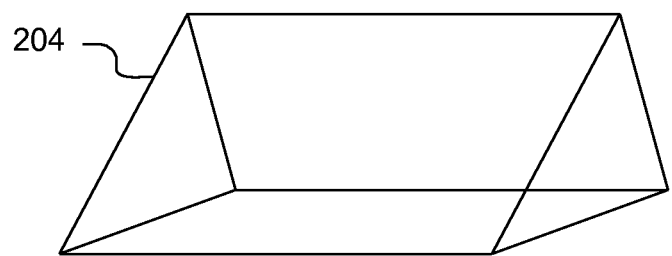
Figure 2C:
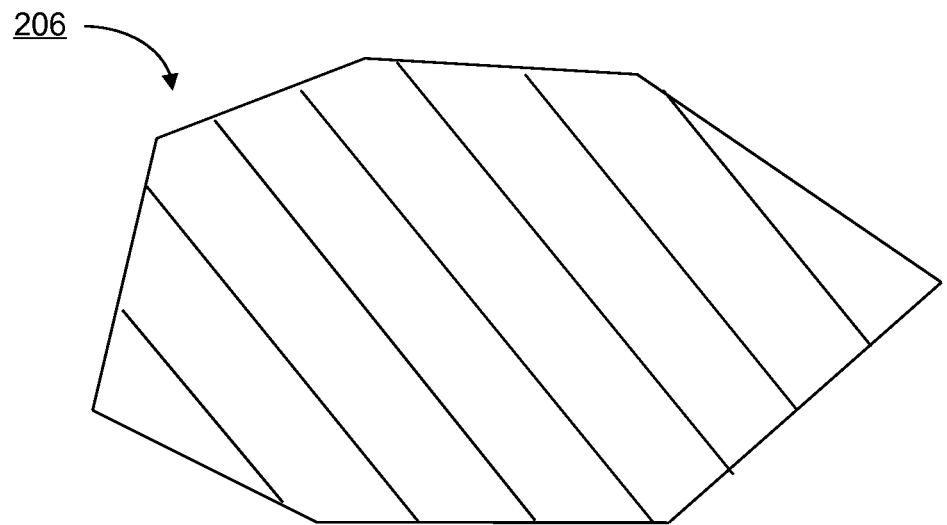
FIG. 2C is a diagram showing a cross-sectional view of another exemplary volume in accordance with one embodiment of the invention.
Figure 2D:
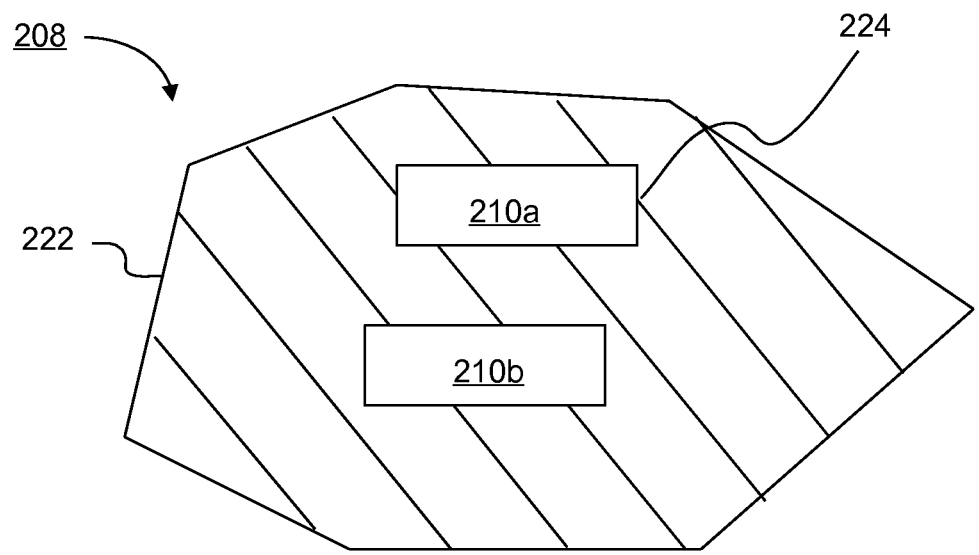
FIG. 2D is a diagram showing a cross-sectional view of yet another exemplary volume containing an interior hole in accordance with one embodiment of the present invention.

Exemplary arbitrarily-shaped volumes include, but are not limited to, a cube 202 (FIG. 2A), a triangular prism 204 (FIG. 2B), and etc. FIG. 2C shows a two-dimensional cross-sectional view 206 of another arbitrarily-shaped volume. According to another embodiment, a two-dimensional cross-sectional view 208 of another volume having one or more interior void spaces 210a-210b is shown in FIG. 2D. It is noted that the volume's boundary can include the external boundary 222 and internal boundary 224 (e.g., boundary of an interior void space).

Figure 3A:
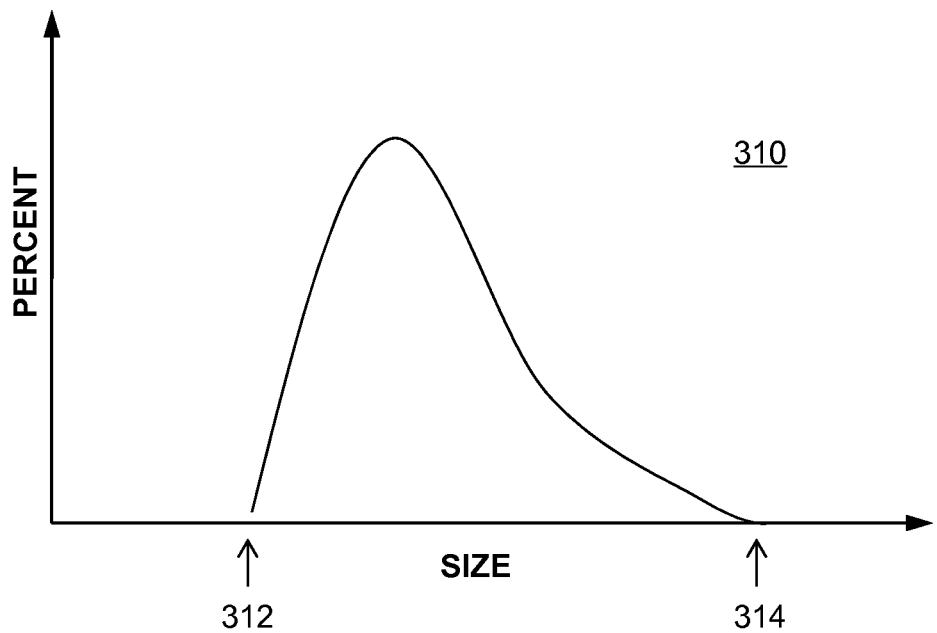
FIG. 3A is a two-dimensional diagram showing a first exemplary characteristic profile of polydisperse spherical particles in accordance with one embodiment of the present invention.
Figure 3B:
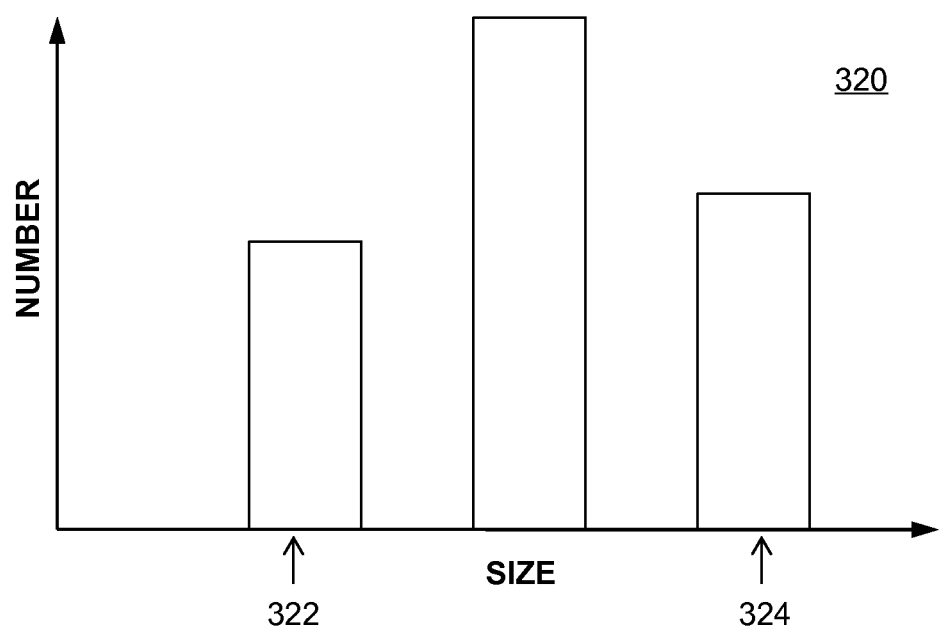
FIG. 3B is a two-dimensional diagram showing a second exemplary characteristic profile of polydisperse spherical particles in accordance with one embodiment of the present invention.

Exemplary characteristic profiles 310, 320 for polydisperse spherical particles are shown in FIGS. 3A-3B. The first characteristic profile is a continuous distribution curve 310 with the minimum size 312 and maximum size 314. The vertical axis represents percentage while the horizontal axis represents size (e.g., diameter of the particle). In FIG. 3B, the characteristic profile is discrete distribution 320. The horizontal axis represents the size of a particle with the minimum size 322 and the maximum size 324. The vertical axis represents number of particles for each particular size.

Referring back to FIG. 1, at step 104, process 100 creates a computerized model with a plurality of polydisperse spherical particles having statistical properties defined in the characteristic profile with steps described below. The plurality of polydisperse spherical particles is generated in accordance with the characteristic profile, such that the generated particles possess the statistical properties defined in the characteristic profile. In one example, the sequence generated is based on the probability distribution (e.g., shown in FIG. 3A). In another example, respective numbers of particular sized particles in a sequence match the definition (e.g., FIG. 3B).

Figure 4:
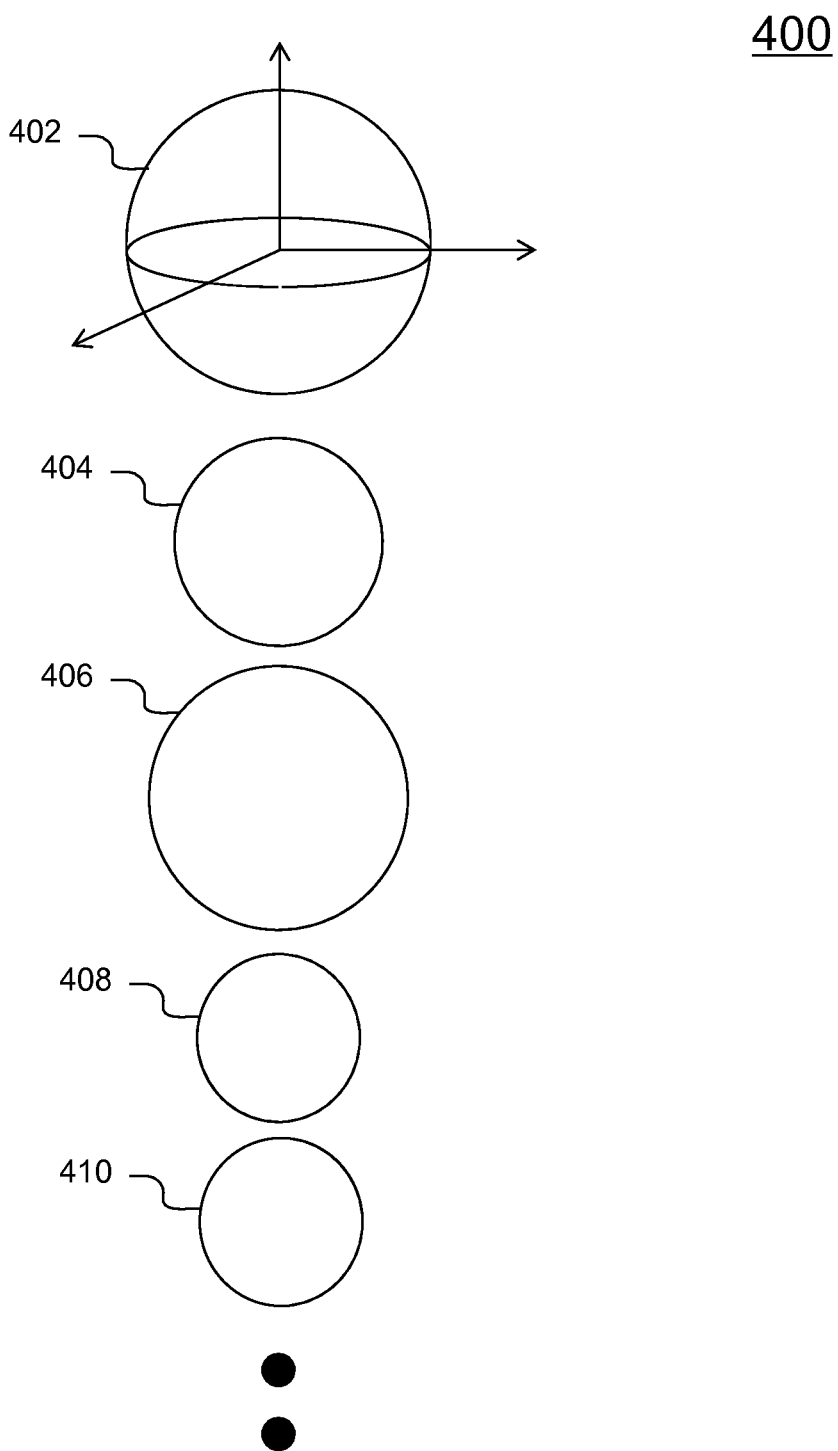
FIG. 4 is a diagram showing an exemplary series of randomly-generated polydisperse spherical particles in accordance with one embodiment of the present invention.

For example, shown in FIG. 4 is an exemplary series 400 of randomly-generated polydisperse spherical particles. The series 400 may be created in accordance with the characteristic profile (e.g., 310, 320) defined by user. Randomness of the generation can be achieved with well-known techniques, for example, employing a series of pseudo-random numbers. Randomly-generated series of polydisperse spherical particles would statistically ensure that the creation of computerized model contain proper amount of different spherical particles defined in the characteristic profile. For illustration simplicity, circles (e.g., 404-410) shown in the figures of this paper represent spherical particles (e.g., sphere 402). The series 400 may be generated on demand, for example, one or a specific number at a time.

At step 106, a border layer is formed by placing or disposing a first portion of the polydisperse spherical particles onto the volume's boundary represented by a plurality of polygons (e.g., FEA mesh model). There is no set limit as to how many polydisperse spherical particles are in the first portion.

Figure 5A:
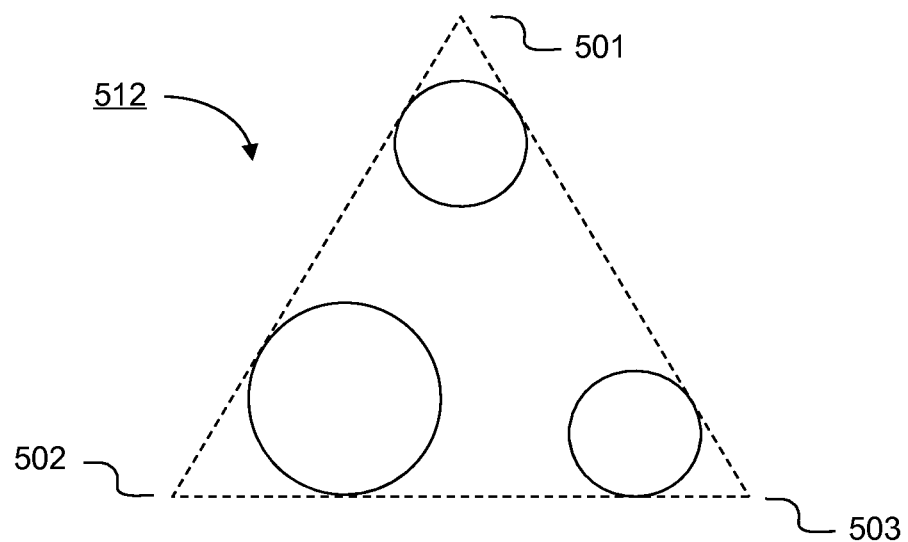
FIG. 5A is a diagram showing an exemplary polygon representing a portion of the boundary of an arbitrarily-shaped volume, according to an embodiment of the present invention.
Figure 5B:
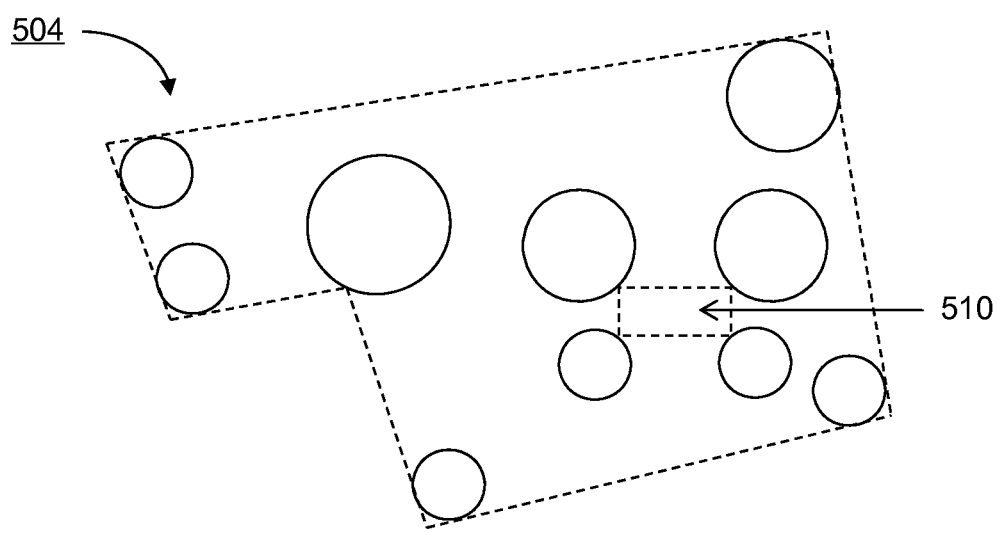
FIG. 5B is a diagram showing a cross-sectional view of an exemplary volume having an interior hole, according to an embodiment of the present invention.

According to one embodiment, the border layer is formed by placing polydisperse spherical particles in the following order: near vertexes of each polygon, along edges of each polygon and then the inner space bounded by already-paced particles within the volume's boundary. FIGS. 5A-5B show two exemplary polygons having spherical particles placed near respective vertexes. A triangle 512 is shown in FIG. 5A, while an irregular polygon 504 with an interior hole 510 is shown in FIG. 5B. Various sizes of spherical particles are shown being placed near vertexes.

Figure 6A:
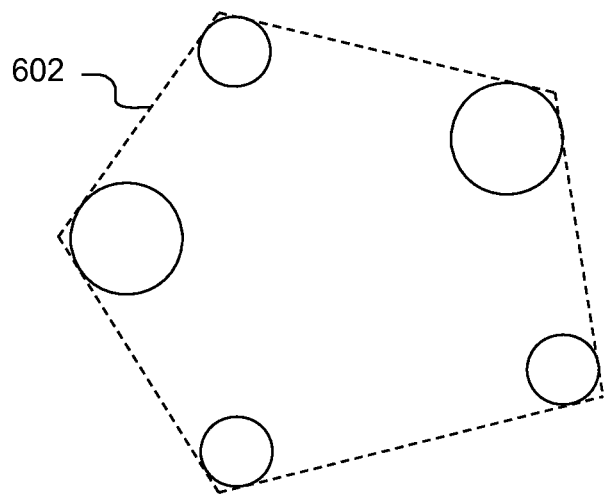
FIGS. 6A-6D are a series of diagrams showing an exemplary sequence of placing polydisperse spherical particles onto a polygon that represents a portion of an arbitrarily-shaped volume's boundary, according to an embodiment of the present invention.
Figure 6B:
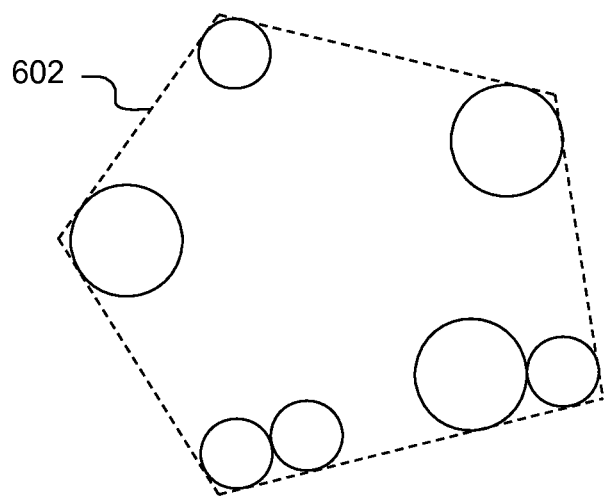
Figure 6C:
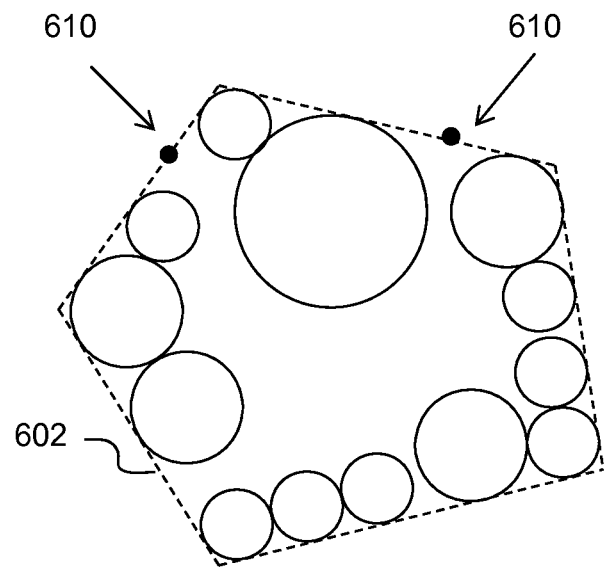
Figure 6D:
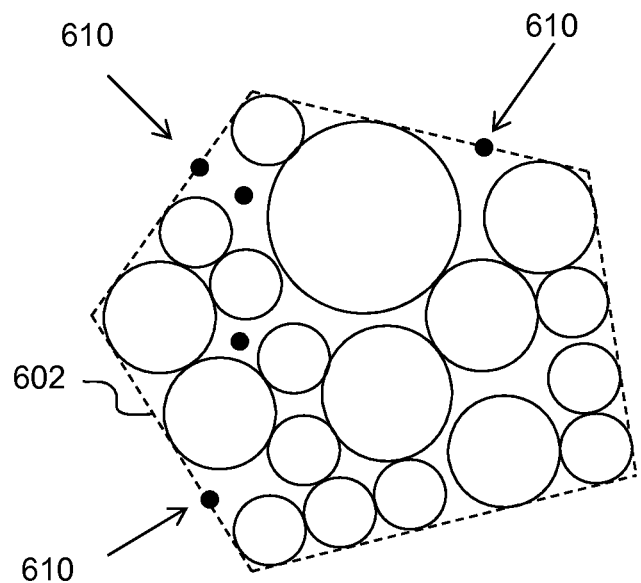

An exemplary sequence of placing the polydisperse spherical particles onto an exemplary polygon 602 is shown in FIGS. 6A-6D. FIG. 6A shows particles are placed near vertexes of the pentagon 602, which is a portion of an arbitrarily-shaped volume. FIG. 6B shows the pentagon 602 having particles partially placed on edges. FIG. 6C shows the pentagon 602 having particles placed on vertexes and edges. FIG. 6D shows particles fully placed on the pentagon 602. According to one embodiment, placing or disposing spherical particles along edges starts from either one of the corresponding vertexes. Power diagrams (described below with an example shown in FIGS. 10C-10G) are used for placement of the spherical particles in forming the border layer.

When forming the border layer, one or more null-sized particles are placed at any hole or space in the border layer. Null-sized particle is a point or zero-diameter sphere (shown as circular dots 610) in FIGS. 6C-6D. Null-sized particles are configured for "sealing" the border layer. With placement of the null-sized particles, all holes or spaces in the border layer are filled or "sealed". In other words, no other spherical particle is allowed to pass through.

Figure 7:
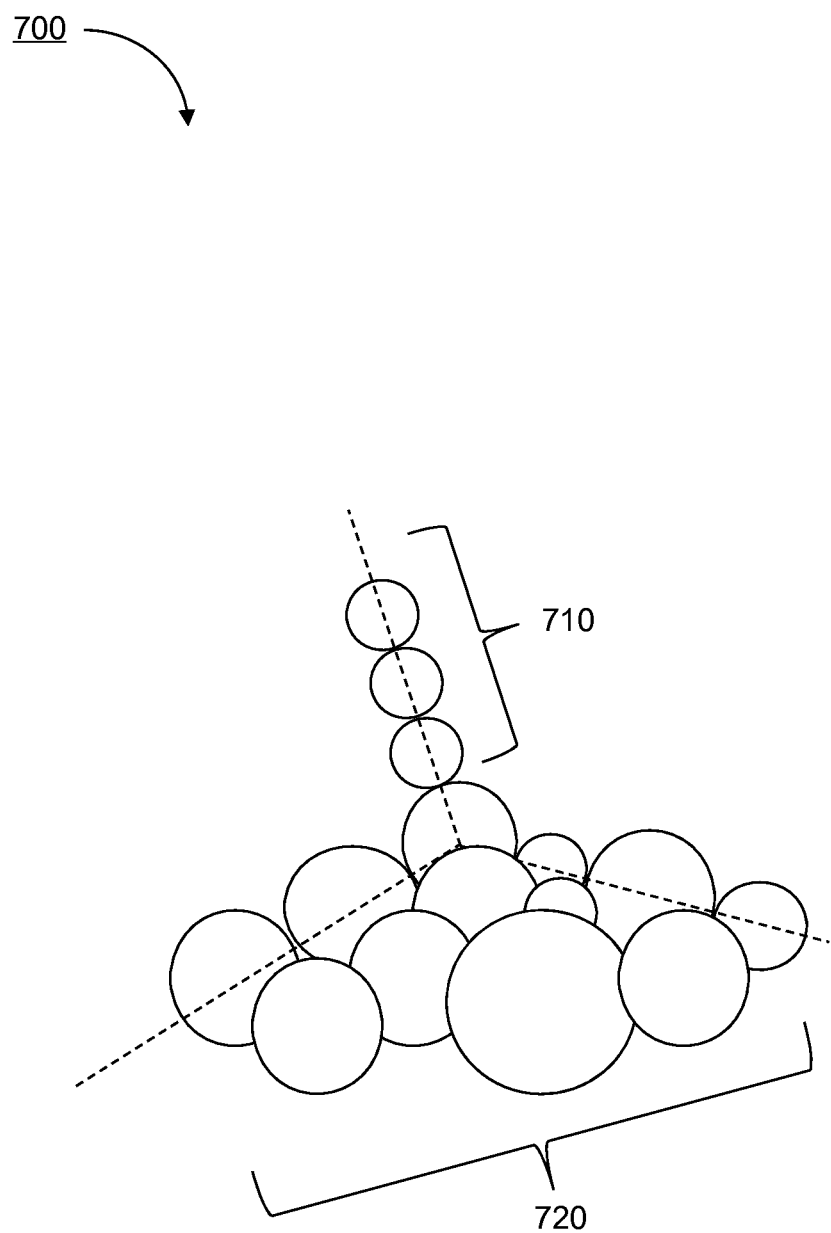
FIG. 7 is a three-dimensional diagram showing one corner of an exemplary border layer in accordance with one embodiment of the present invention.

Generally, a border layer comprises polydisperse spherical particles disposed or placed onto a plurality of polygons that represents the volume's boundary. FIG. 7 is a three-dimensional view showing an exemplary partial border layer 700 of a computerized model, according to an embodiment of the present invention. For illustration simplicity, only few spherical particles are shown. One having ordinary skill in the art would know that a border layer contains more than just few shown in FIG. 7, which includes a number of polydisperse spherical particles 720 disposed on one polygon, and other spherical particles 710 along an edge of another polygon.

Referring back to FIG. 1, at step 108, a second portion of the polydisperse spherical particles are used for filling up an interior space surrounded by the border layer in a layer-to-layer scheme, which starts from the border layer then moves inwards until the interior space has been filled up. Each of the particles is allowed to pass or "leak" through holes in the current layer towards the border layer.

Figure 8:
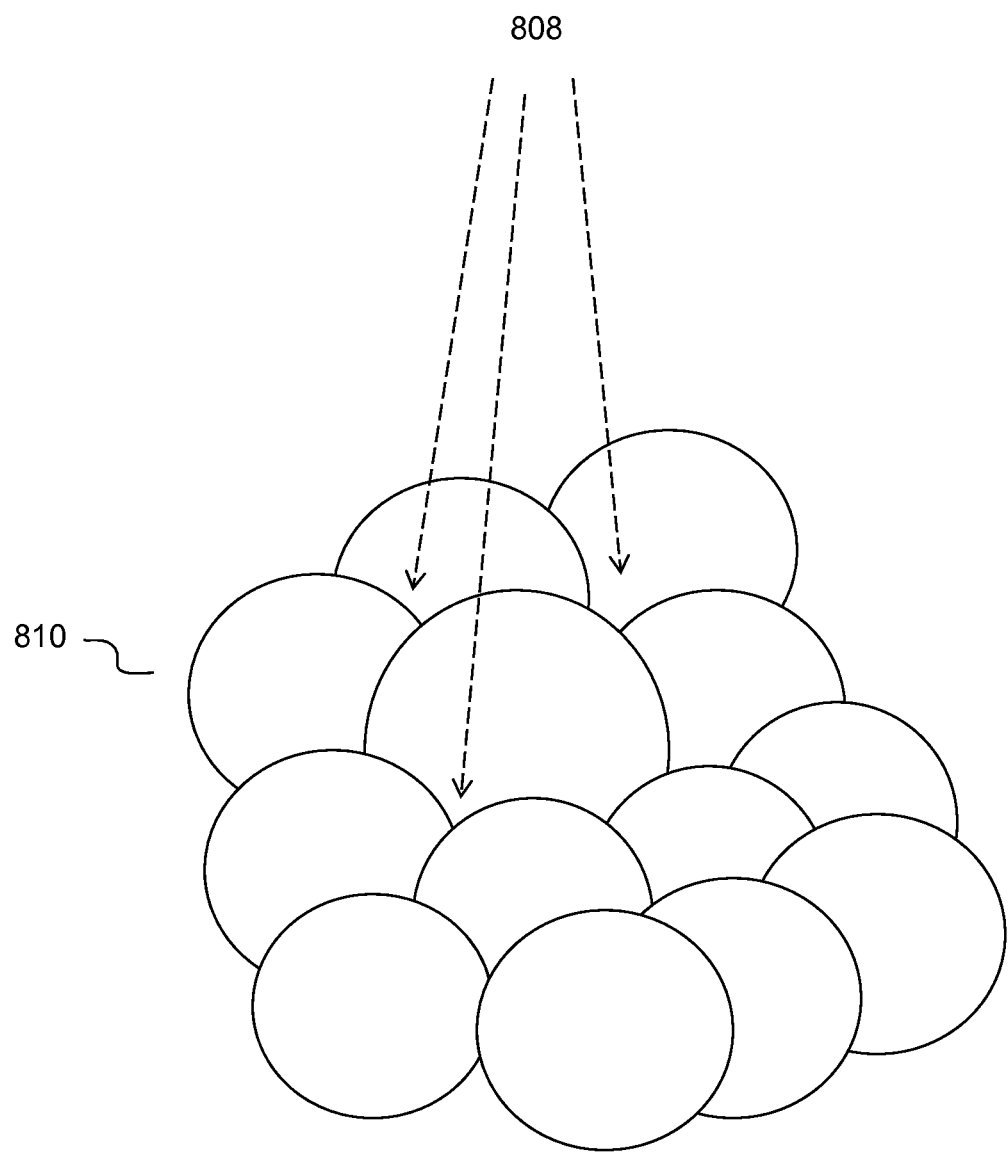
FIG. 8 is a diagram showing exemplary candidate locations identified using power diagrams, according an embodiment of the present invention.

The layer-to-layer scheme includes searching a best suitable location from a list of candidate locations. Candidate locations are identified using three-dimension power diagrams and ranked by respective sizes of the candidate locations. FIG. 8 shows a number of exemplary candidate locations 808 (pointed by dotted line arrows), which are identified using power diagrams (not shown in FIG. 8) from a layer 810. Each of the candidate locations is associated with a maximum possible size at that location.

Figure 9:
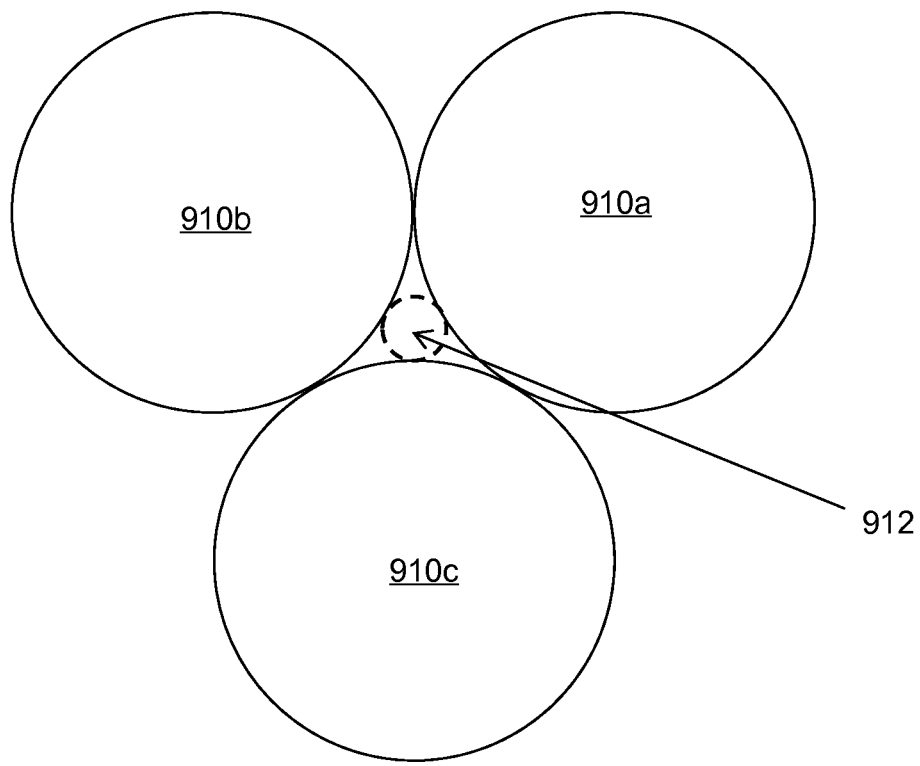
FIG. 9 is a diagram showing exemplary orientations of polydisperse spherical particles having hole that allows a spherical particle passing through, according to an embodiment of the present invention.
Figure 9:
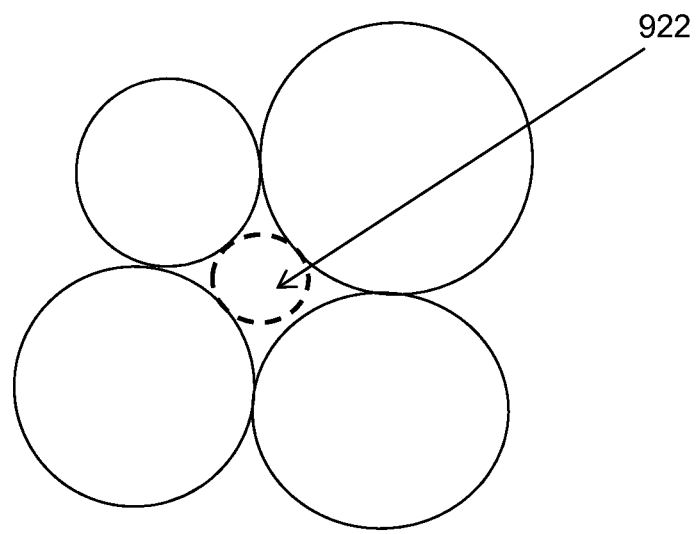

FIG. 9 is a two-dimensional view shows exemplary holes that can be passed through during the filling up the interior space operation. A hole 922 is located among four particles, while hole 912 is located among three identical particles 910$a$-910$c$. The best possible location for filling up operation is among three identical particles 910$a$-910$c$, because the particles are packed in maximum occupancy or with minimum unoccupied space. For those having ordinary skill in the art would know that four identical spherical particles provide best efficiency in three-dimension. When hole 912 or 922 is large enough, a particular spherical particle is allowed to pass through the hole towards the border layer.

The "pass through" operation is configured for allowing better usage of the space thereby achieving higher packing density. In other words, in the layer-to-layer scheme of filling up the interior space, any spherical particle is allowed to pass through the current layer towards the border layer. And no spherical particle can pass through the border layer because the border layer has been "sealed" with null-sized particles hence impenetrable. In one embodiment, the border layer is designated as "level-0", which subsequent layers are denoted as "level-1", "level-2", etc. Spherical particles are allowed to pass through or "leak" from high numbered level to lower ones only. And no particle is allowed to pass or "leak" through "level-0".

It is also noted that levels or layers are dynamically formed. In other words, as each particle is placed on a current layer, the current layer will be updated to become a new current layer. The list of candidate locations is updated accordingly using power diagrams.

Figure 10A:
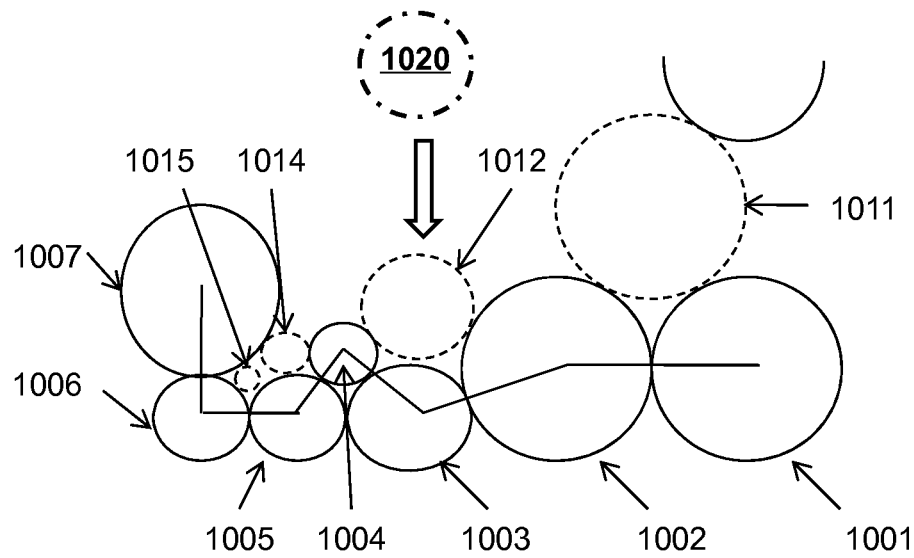
FIGS. 10A and 10B are diagrams showing exemplary searching and placement of spherical particles using power diagrams, according to an embodiment of the present invention.
Figure 10A:
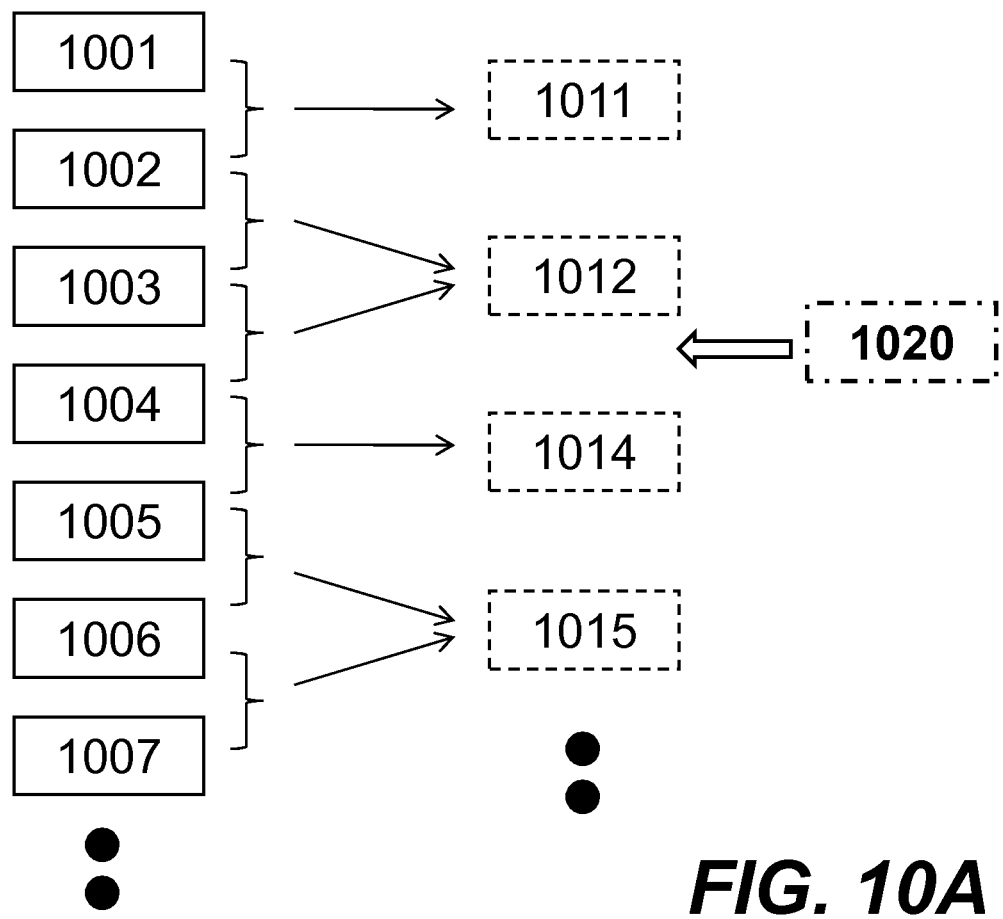
Figure 10B:
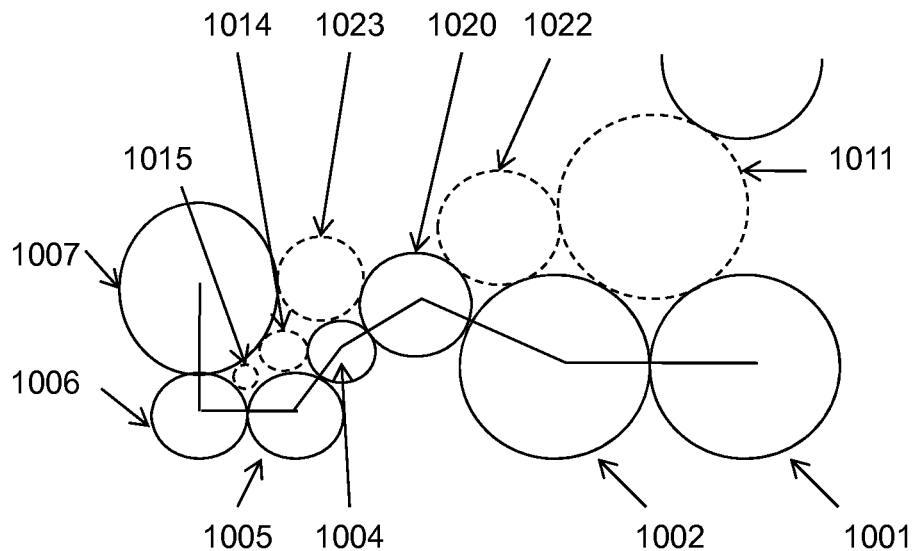
Figure 10B:
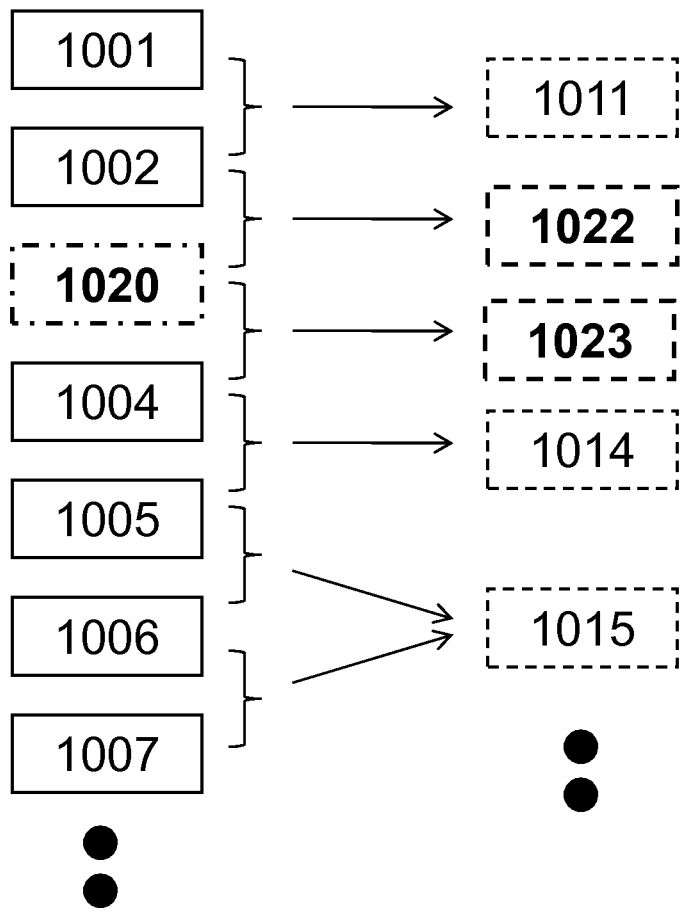

To demonstrate how power diagrams are used for identifying a list of candidate locations, a two-dimensional example is collectively shown in FIGS. 10A and 10B. Those of ordinary skill in the art would know how three-dimensional power diagrams (not shown) employ substantially similar principles.

In FIG. 10A, seven solid line circles 1001-1007 form a current layer (it starts from a border layer). Candidate locations are shown as dotted line circles 1011, 1012, 1014 and 1015. Using power diagrams, candidate location 1011 is for existed circle pair 1001 and 1002. Candidate location 1012 is for circle pairs 1002-1003 and 1003-1004, because power diagrams of both pairs indicate the same candidate location 1012. Similarly, candidate location 1014 is for circle pair 1004-1005, and candidate location 1015 is shared by circle pairs 1005-1006 and 1006-1007.

In one embodiment, the candidate locations 1011-1015 are ranked by respective sizes to accommodate a search (i.e., searching a best suitable location). In FIG. 10A, the size-ranked list is candidates 1011, 1012, 1014 and 1015 in descending order in terms of size. One having ordinary skill of the art would know that the order can be reversed (i.e., ascending order) to achieve the same. Also the example is arbitrary, there can be unlimited number of possibility in terms of different sizes defined in the characteristic profile.

In one embodiment, at step 108 of process 100, each of the second portion of the polydisperse spherical particles is compared with the size-ranked candidate list to determine which location is the best suitable. Shown in FIG. 10A, a circle 1020 is placed in a best suitable location 1012. The search can be performed with well known methods, for example, searching a location in the size-ranked candidate list using its size (e.g., diameter).

After the circle 1020 has been placed, the current layer is changed (solid line circles 1001, 1002, 1020, 1004, 1005, 1006 and 1007 shown in FIG. 10B). Two new candidate locations 1022, 1023 are established. A correlation between circle pair and candidate location has also changed (shown in lower portion of FIG. 10B).

It is noted that example shown in FIGS. 10A-10B indicates searching a best suitable location is a localized operation even in a very large model. Only the neighboring candidate locations are required to be searched. Furthermore, power diagrams provide not only the information with respect to largest potential size at a given location, but neighboring information that enables optimal placement in terms of desired packing requirements, including but not limited to, packing density, particle distribution in terms of location and size.

Figure 10C:
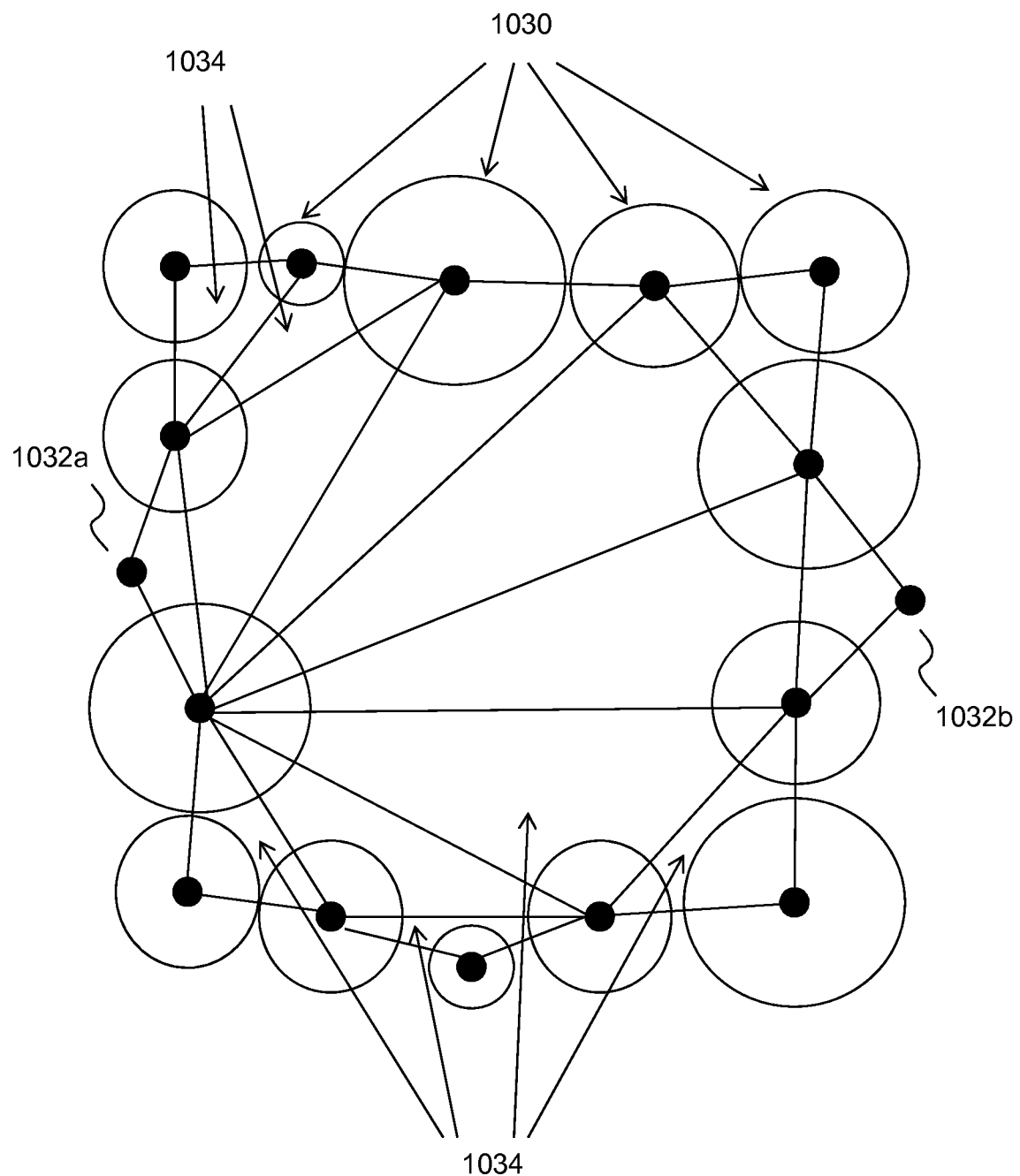
FIGS. 10C-10G are diagrams showing exemplary power diagrams in accordance with one embodiment of the present invention.
Figure 10D:
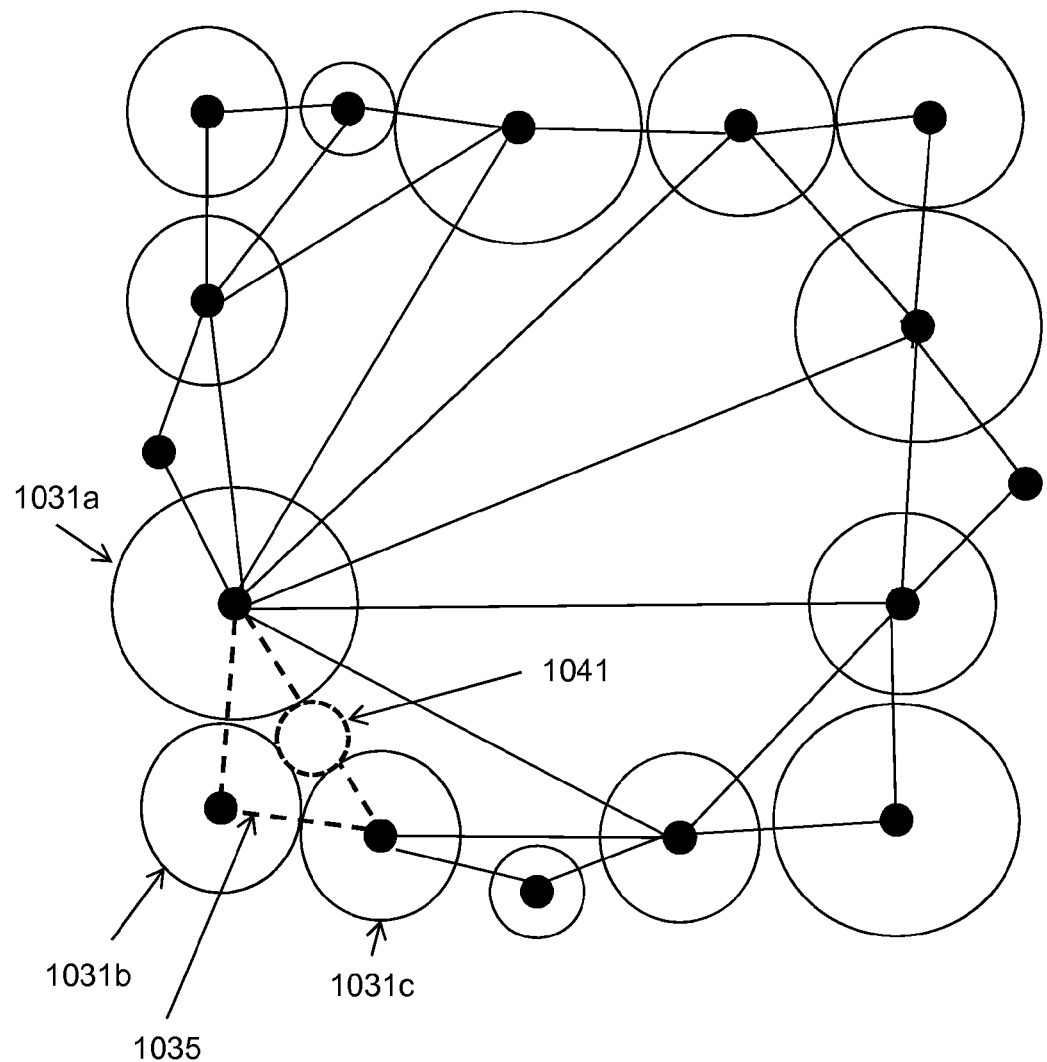
Figure 10E:
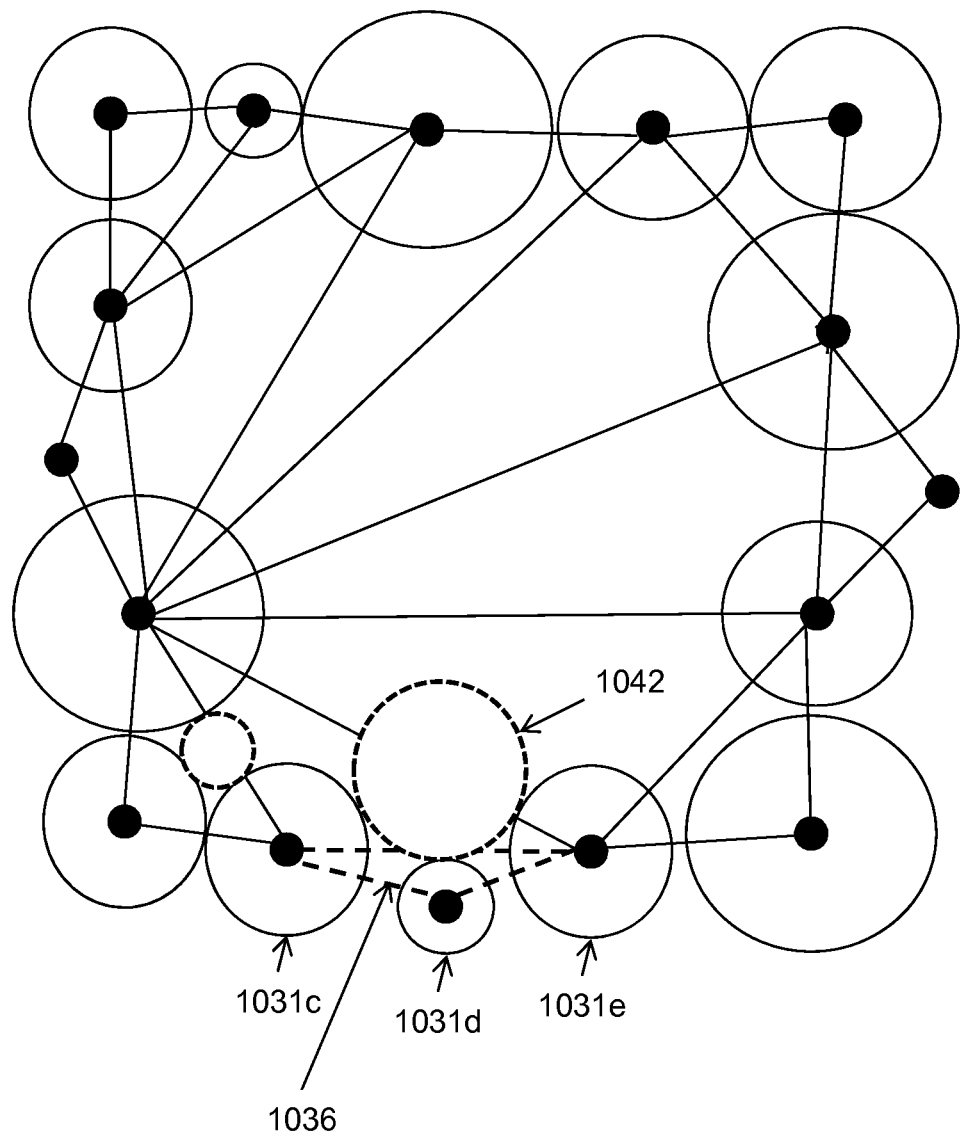

To further demonstrate how power diagrams work, another two-dimensional example shows in FIGS. 10C-10G. In FIG. 10C, a layer of polydisperse spherical particles 1030 forming an outer layer (e.g., a border layer). It is noted that null-sized particles 1032a-1032b are shown as dots. Each of the particles 1030 is shown a center (shown as black dot within each circle). Power diagrams 1034 are shown as triangles connecting respective centers of three circles. Each power diagram 1034 represents a candidate location for maximum possible size circle (or sphere in 3-D). FIG. 10D shows a first exemplary power diagram 1035 for three particles 1031a, 1031b and 1031c. The candidate location and associated size is shown as a dotted line circle 1041. A second exemplary power diagram 1036 for particles 1031c, 1031d and 1031e is shown in FIG. 10E. Candidate location and associated size is shown as dotted line circle 1042.

It is noted that both first and second exemplary power diagrams 1035-1036 have two of the three sides or edges on the border. For power diagram 1035, the side between particles 1031a and 1031b, and the side between particles 1031b and 1031c are on the border. For power diagram 1036, the side between particles 1031c and 1031d, and the side between particles 1031d and 1031e are on the border.

Figure 10F:
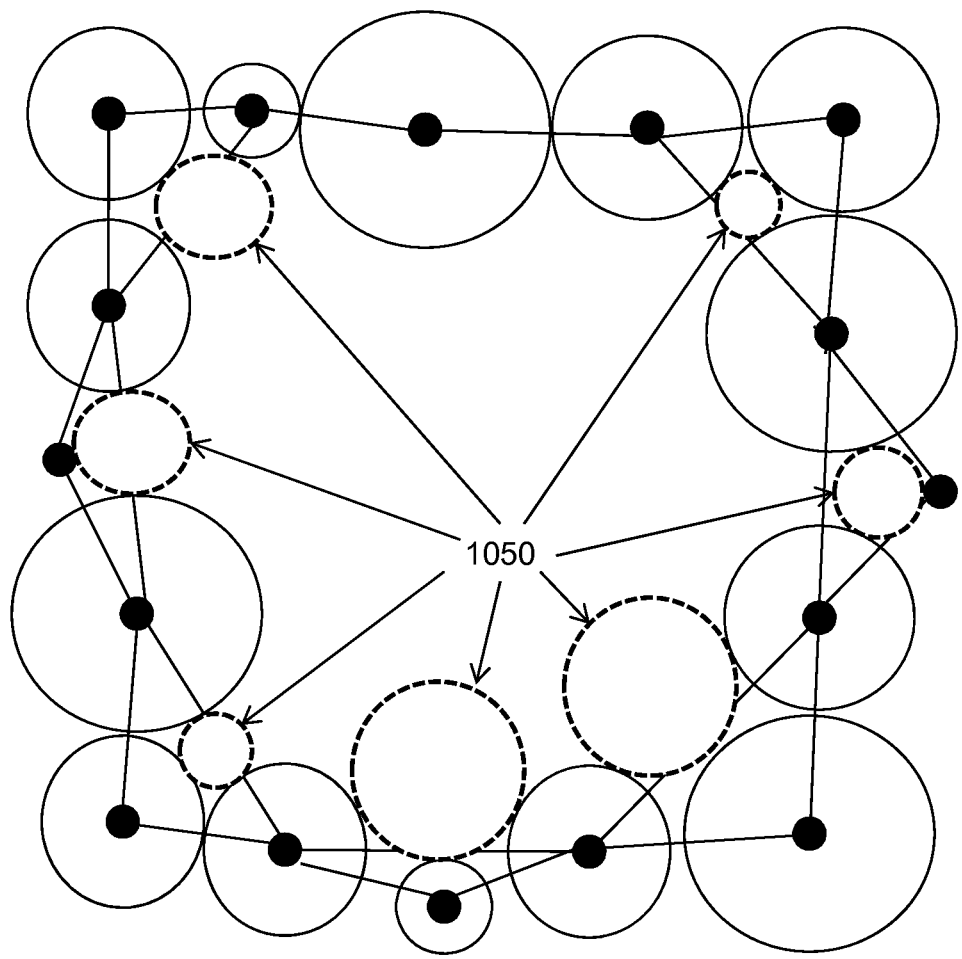

Dotted line circles 1050 shown in FIG. 10F are all candidate locations and associated sizes for power diagrams having two sides on the border. For illustration clarity, internal lines of power diagrams are not shown in FIG. 10F.

Figure 10G:
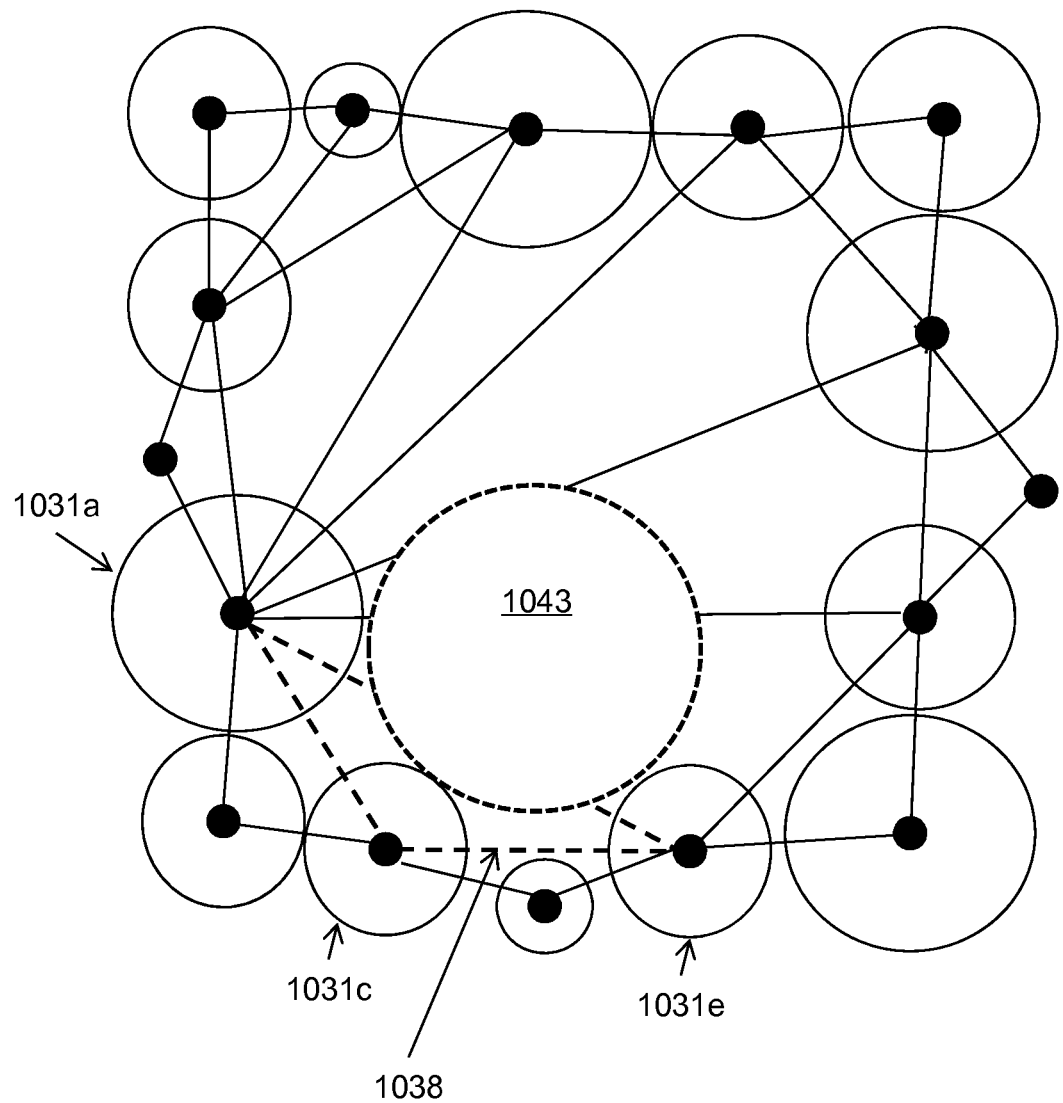

In FIG. 10G, a power diagram 1038 for particles 1031a, 1031c and 1031e is shown having a candidate location and associated size (dotted line circle 1043). It is noted that the power diagram 1038 only has one side at the border (between particles 1031c and 1031e). All candidate locations in each layer are identified and ranked by respective sizes, such that any given particles of the second portion can be placed in a best suitable location (e.g., searching through a ranked list). Once the given particle is placed, the current layer and the corresponding list of candidate locations are updated accordingly.

Finally, searching for a best suitable location is performed using three-dimensional power diagrams (i.e., tetrahedron) with directionality to ensure each candidate location is located within the volume's boundary. The present invention allows a volume having external and internal boundaries.

After the interior space has been filled up, process 100 moves to step 110, in which an optional adjustment of the computerized model is performed to achieve a desired packing requirements defined by users. In one example, particles in a computerized model may be culled to achieve desired packing requirements (e.g., simulating porous material). In another example, a computerized model contains gaps that can be filled with certain smaller particles (e.g., mixing concrete). Term "Gaps" is used herein for a space between particles that are generally too small to be filled with the minimum size particle defined in the characteristic profile. In yet another example, particles in a computerized model may be adjusted to have slightly different size or location (e.g., achieving different packing density). Process 100 ends thereafter, which means that the computerized model has been created.

Figure 11:
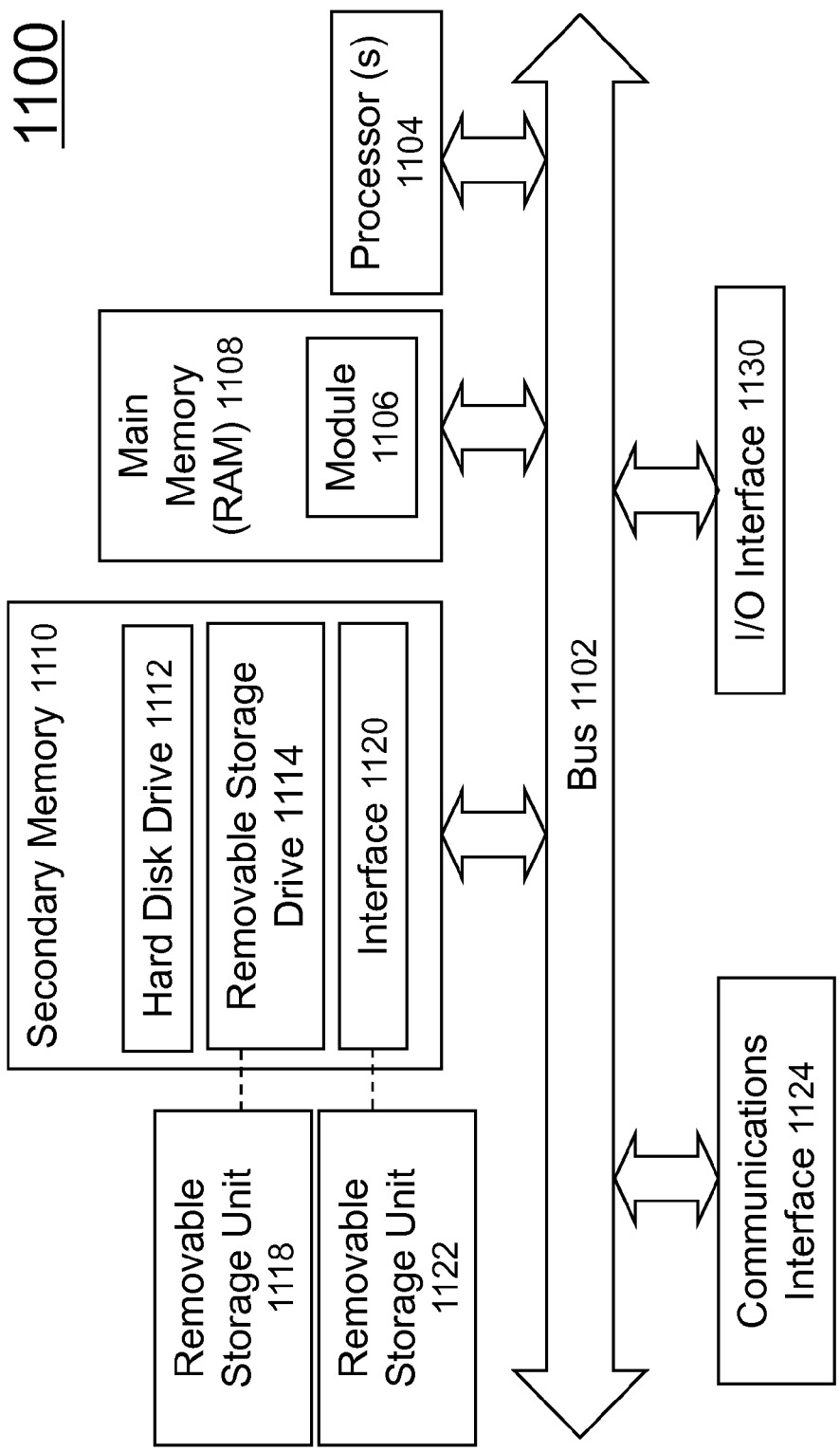
FIG. 11 is a function diagram showing salient components of an exemplary computer system, in which an embodiment of the present invention may be implemented.

According to one aspect, the present invention is directed towards one or more computer systems capable of carrying out the functionality described herein. An example of a computer system 1100 is shown in FIG. 11. The computer system 1100 includes one or more processors, such as processor 1104. The processor 1104 is connected to a computer system internal communication bus 1102. Various software embodiments are described in terms of this exemplary computer system. After reading this description, it will become apparent to a person skilled in the relevant art(s) how to implement the invention using other computer systems and/or computer architectures.

Computer system 1100 also includes a main memory 1108, preferably random access memory (RAM), and may also include a secondary memory 1110. The secondary memory 1110 may include, for example, one or more hard disk drives 1112 and/or one or more removable storage drives 1114, representing a floppy disk drive, a magnetic tape drive, an optical disk drive, etc. The removable storage drive 1114 reads from and/or writes to a removable storage unit 1118 in a well-known manner. Removable storage unit 1118, represents a floppy disk, magnetic tape, optical disk, etc. which is read by and written to by removable storage drive 1114. As will be appreciated, the removable storage unit 1118 includes a computer usable storage medium having stored therein computer software and/or data.

In alternative embodiments, secondary memory 1110 may include other similar means for allowing computer programs or other instructions to be loaded into computer system 1100. Such means may include, for example, a removable storage unit 1122 and an interface 1120. Examples of such may include a program cartridge and cartridge interface (such as that found in video game devices), a removable memory chip (such as an Erasable Programmable Read-Only Memory (EPROM), Universal Serial Bus (USB) flash memory, or PROM) and associated socket, and other removable storage units 1122 and interfaces 1120 which allow software and data to be transferred from the removable storage unit 1122 to computer system 1100. In general, Computer system 1100 is controlled and coordinated by operating system (OS) software, which performs tasks such as process scheduling, memory management, networking and I/O services.

There may also be a communications interface 1124 connecting to the bus 1102. Communications interface 1124 allows software and data to be transferred between computer system 1100 and external devices. Examples of communications interface 1124 may include a modem, a network interface (such as an Ethernet card), a communications port, a Personal Computer Memory Card International Association (PCMCIA) slot and card, etc. The computer 1100 communicates with other computing devices over a data network based on a special set of rules (i.e., a protocol). One of the common protocols is TCP/IP (Transmission Control Protocol/Internet Protocol) commonly used in the Internet. In general, the communication interface 1124 manages the assembling of a data file into smaller packets that are transmitted over the data network or reassembles received packets into the original data file. In addition, the communication interface 1124 handles the address part of each packet so that it gets to the right destination or intercepts packets destined for the computer 1100. In this document, the terms "computer program medium" and "computer usable medium" are used to generally refer to media such as removable storage drive 1114, and/or a hard disk installed in hard disk drive 1112. These computer program products are means for providing software to computer system 1100. The invention is directed to such computer program products.

The computer system 1100 may also include an input/output (I/O) interface 1130, which provides the computer system 1100 to access monitor, keyboard, mouse, printer, scanner, plotter, and alike.

Computer programs (also called computer control logic) are stored as application modules 1106 in main memory 1108 and/or secondary memory 1110. Computer programs may also be received via communications interface 1124. Such computer programs, when executed, enable the computer system 1100 to perform the features of the present invention as discussed herein. In particular, the computer programs, when executed, enable the processor 1104 to perform features of the present invention. Accordingly, such computer programs represent controllers of the computer system 1100.

In an embodiment where the invention is implemented using software, the software may be stored in a computer program product and loaded into computer system 1100 using removable storage drive 1114, hard drive 1112, or communications interface 1124. The application module 1106, when executed by the processor 1104, causes the processor 1104 to perform the functions of the invention as described herein.

The main memory 1108 may be loaded with one or more application modules 1106 that can be executed by one or more processors 1104 with or without a user input through the I/O interface 1130 to achieve desired tasks. In operation, when at least one processor 1104 executes one of the application modules 1106, the results are computed and stored in the secondary memory 1110 (i.e., hard disk drive 1112). The status of the finite element analysis is reported to the user via the I/O interface 1130 either in a text or in a graphical representation. In one embodiment, an application module 1106 is configured to facilitate the creation of a computerized model having a plurality of polydisperse spherical particles.

Although the present invention has been described with reference to specific embodiments thereof, these embodiments are merely illustrative, and not restrictive of, the present invention. Various modifications or changes to the specifically disclosed exemplary embodiments will be suggested to persons skilled in the art. For example, whereas two-dimensional diagrams have been generally shown, the present invention is directed to three-dimensional polydisperse spherical particles, circles can be treated as spheres. In summary, the scope of the invention should not be restricted to the specific exemplary embodiments disclosed herein, and all modifications that are readily suggested to those of ordinary skill in the art should be included within the spirit and purview of this application and scope of the appended claims.

I claim:

1. A method of creating a computerized model containing polydisperse spherical particles packed in an arbitrarily-shaped volume, said method comprising:
    receiving, in a computer system, a definition of an arbitrarily-shaped volume and a characteristic profile of a plurality of polydisperse spherical particles, said definition comprising at least four polygons representing the volume's boundary;
    creating a computerized model containing the plurality of polydisperse spherical particles having statistical properties defined in the characteristic profile with steps of:
    forming a border layer within the volume's boundary using a first portion of the plurality of polydisperse spherical particles, said border layer being disposed onto the polygons;
    sealing one or more holes in said border layer with one or more null-sized particles during said forming the border layer; and
    filling up an interior space surrounded by said border layer using a second portion of the sequence of polydisperse spherical particles with a layer-by-layer scheme from said border layer inwards, said layer-by-layer scheme comprises searching a best suitable location for each of said second portion of the plurality of polydisperse spherical particles from a list of candidate locations, which are identified using power diagrams and ranked by respective sizes of said candidate locations, wherein said each of the second portion of the plurality of polydisperse spherical particles is allowed to pass through holes in a current layer towards said border layer when possible.

2. The method of claim 1, wherein the volume's boundary comprises an outer boundary of the volume.

3. The method of claim 2, wherein the volume's boundary comprises one or more inner boundaries of the volume.

4. The method of claim 1, wherein said characteristic profile comprises minimum and maximum sizes, and a size distribution of said polydisperse spherical particles.

5. The method of claim 4, wherein said size distribution is a discrete distribution for fixed number of sizes between the minimum and the maximum sizes.

6. The method of claim 4, wherein said size distribution is a continuous distribution between the minimum and the maximum sizes.

7. The method of claim 1, wherein each polygon comprises a directionality property for indicating which side of said each polygon is inside the volume.

8. The method of claim 1, wherein said first portion and said second portion of the plurality of polydisperse spherical particles are randomly generated in accordance with the characteristic profile such that the plurality of polydisperse spherical particles possesses statistical properties defined in the characteristic profile.

9. The method of claim 1, wherein said forming the border layer further comprises placing said first portion of the plurality of polydisperse spherical particles near vertex of each polygon, then along edges of said each polygon and in an inner space bounded by already-placed spherical particles.

10. The method of claim 1, wherein said list of candidate locations comprises neighbor information.

11. A non-transitory computer readable storage medium containing computer executable instructions which, when executed in a computer system, perform a method of creating a computerized model containing polydisperse spherical particles packed in an arbitrarily-shaped volume, said method comprising:
    receiving, in a computer system, a definition of an arbitrarily-shaped volume and a characteristic profile of a plurality of polydisperse spherical particles, said definition comprising at least four polygons representing the volume's boundary;
    creating a computerized model containing the plurality of polydisperse spherical particles having statistical properties defined in the characteristic profile with steps of:
    forming a border layer within the volume's boundary using a first portion of the plurality of polydisperse spherical particles, said border layer being disposed onto the polygons;
    sealing one or more holes in said border layer with one or more null-sized particles during said forming the border layer; and
    filling up an interior space surrounded by said border layer using a second portion of the sequence of polydisperse spherical particles with a layer-by-layer scheme from said border layer inwards, said layer-by-layer scheme comprises searching a best suitable location for each of said second portion of the plurality of polydisperse spherical particles from a list of candidate locations, which are identified using power diagrams and ranked by respective sizes of said candidate locations, wherein said each of the second portion of the plurality of polydisperse spherical particles is allowed to pass through holes in a current layer towards said border layer when possible.

12. The non-transitory computer readable storage medium of claim 11, wherein said forming the border layer further comprises placing said first portion of the plurality of polydisperse spherical particles near vertex of each polygon, then along edges of said each polygon and in an inner space bounded by already-placed spherical particles.

13. A system of creating a computerized model containing polydisperse spherical particles packed in an arbitrarily-shaped volume, said system comprising:

a main memory for storing computer readable code for an application module;

at least one processor coupled to the main memory, said at least one processor executing the computer readable code in the main memory to cause the application module to perform operations by a method of:

receiving a definition of an arbitrarily-shaped volume and a characteristic profile of a plurality of polydisperse spherical particles, said definition comprising at least four polygons representing the volume's boundary;

creating a computerized model containing the plurality of polydisperse spherical particles having statistical properties defined in the characteristic profile with steps of:

forming a border layer within the volume's boundary using a first portion of the plurality of polydisperse spherical particles, said border layer being disposed onto the polygons;

sealing one or more holes in said border layer with one or more null-sized particles during said forming the border layer; and filling up an interior space surrounded by said border layer using a second portion of the sequence of polydisperse spherical particles with a layer-by-layer scheme from said border layer inwards, said layer-by-layer scheme comprises searching a best suitable location for each of said second portion of the plurality of polydisperse spherical particles from a list of candidate locations, which are identified using power diagrams and ranked by respective sizes of said candidate locations, wherein said each of the second portion of the plurality of polydisperse spherical particles is allowed to pass through holes in a current layer towards said border layer when possible.

14. The system of claim 13, wherein said forming the border layer further comprises placing said first portion of the plurality of polydisperse spherical particles near vertex of each polygon, then along edges of said each polygon and in an inner space bounded by already-placed spherical particles.

* * * * *